(12) United States Patent
Hu et al.

(10) Patent No.: US 11,930,751 B2
(45) Date of Patent: Mar. 19, 2024

(54) **POLLEN CONTROL DRY POLLINATION MACHINE FOR *ABIES ZIYUANENSIS***

(71) Applicant: Guangxi Institute of Botany, Guangxi Zhuang Autonomous Region and Chinese Academy of Sciences, Guilin (CN)

(72) Inventors: Xinghua Hu, Guilin (CN); Tao Deng, Guilin (CN); Jiatong Ye, Guilin (CN); Sha Li, Guilin (CN); Xiaozhen Zhu, Guilin (CN); Shixun Huang, Guilin (CN)

(73) Assignee: GUANGXI INSTITUTE OF BOTANY, GUANGXI ZHUANG AUTONOMOUS REGION AND CHINESE ACADEMY OF SCIENCES, Guilin (CN)

( * ) Notice: Subject to any disclaimer, the term of this patent is extended or adjusted under 35 U.S.C. 154(b) by 0 days.

(21) Appl. No.: 18/062,188

(22) Filed: Dec. 6, 2022

(65) Prior Publication Data
US 2023/0225270 A1 Jul. 20, 2023

(30) Foreign Application Priority Data
Jan. 19, 2022 (CN) .......................... 202210060272.5

(51) Int. Cl.
*A01H 1/02* (2006.01)
(52) U.S. Cl.
CPC .................................. *A01H 1/027* (2021.01)
(58) Field of Classification Search
CPC ................................................... A01H 1/027
See application file for complete search history.

(56) References Cited

U.S. PATENT DOCUMENTS 3,943,660 A * 3/1976 Hosaka ................. A01H 1/027
47/1.41

FOREIGN PATENT DOCUMENTS

| CN | 106818464 A | * | 6/2017 | |
| CN | 108450324 A | * | 8/2018 | ............. A01H 1/025 |
| CN | 108651271 A | | 10/2018 | |
| CN | 108668888 A | * | 10/2018 | ............. A01H 1/025 |
| CN | 109168874 A | | 1/2019 | |
| CN | 212087476 U | | 12/2020 | |

(Continued)

OTHER PUBLICATIONS

First Office Action issued in counterpart Chinese Patent Application No. 202210060272.5, dated May 25, 2022.

*Primary Examiner* — Son T Nguyen
(74) *Attorney, Agent, or Firm* — Rachel Pilloff; Sean Passino; Pilloff Passino & Cosenza LLP

(57) ABSTRACT

Disclosed is a pollen control dry pollination machine for *Abies ziyuanensis*, comprising a lever; a side of a top of the lever is fixedly connected with one end of a square tube; another end of the square tube is rotatably connected with a pollination shell; a top of the square tube and a top of the pollination shell are slidably connected with a fan; the pollination shell is internally provided with a pollen box, a pollen outlet cover and a pollination chamber from a top to a bottom in sequence; the pollen box is communicated with the pollen outlet cover; a bottom of the pollination chamber is provided with an opening; an *Abies ziyuanensis* ovulate strobilus to be pollinated is placed in the pollination chamber; a bottom of the pollination shell is fixedly connected with a rotating opening; the lever is provided with a switch.

1 Claim, 9 Drawing Sheets

(56) References Cited

FOREIGN PATENT DOCUMENTS

Figure 1:
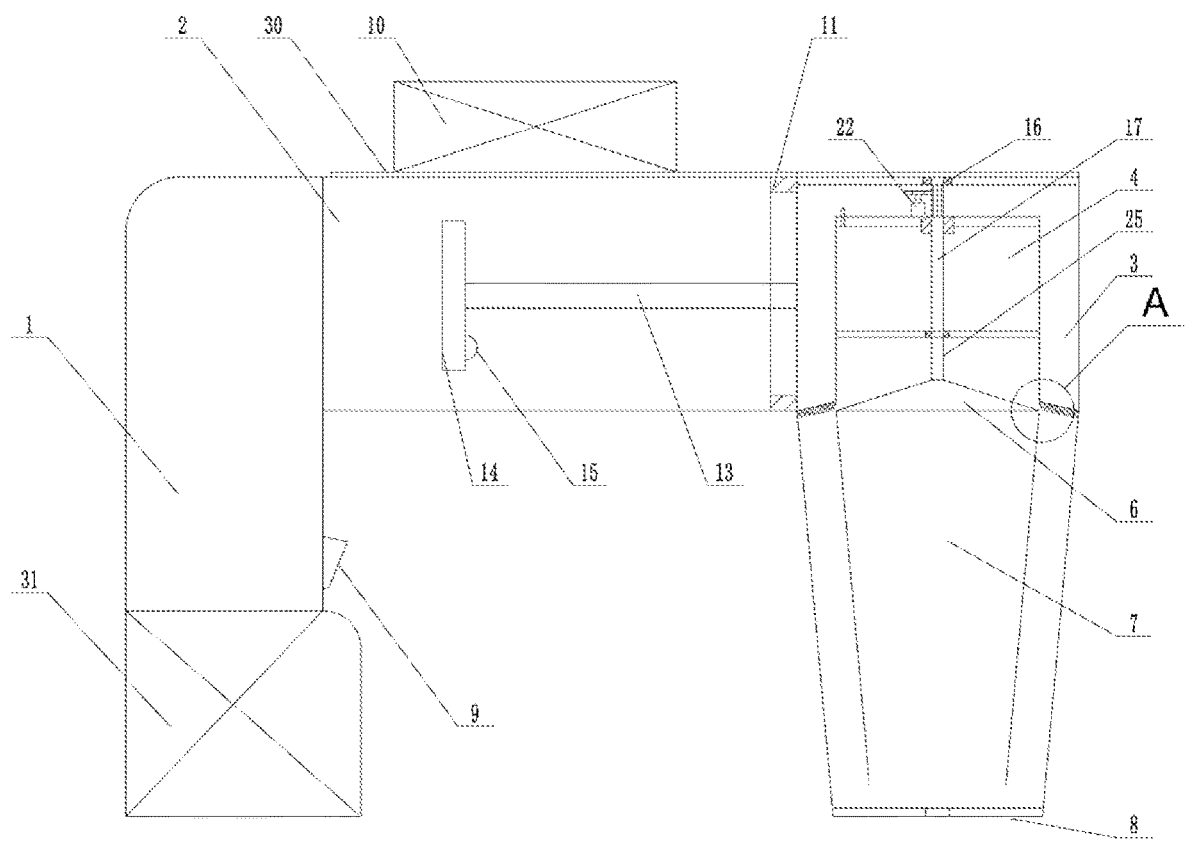
Figure 2:
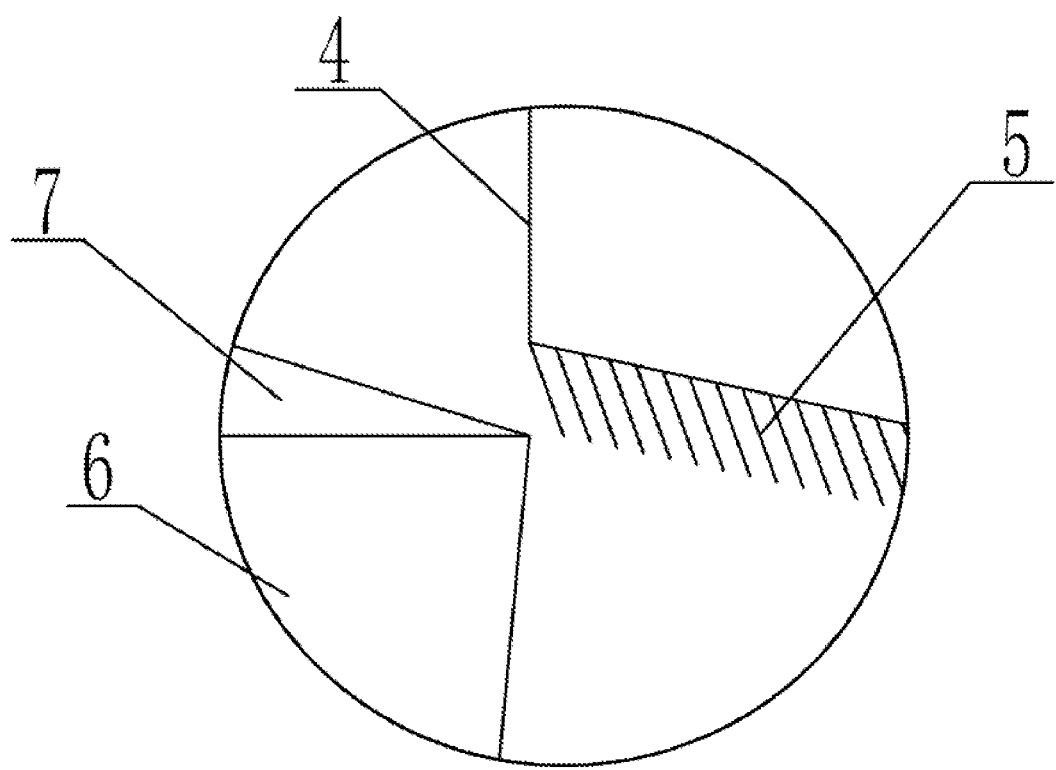
Figure 3:
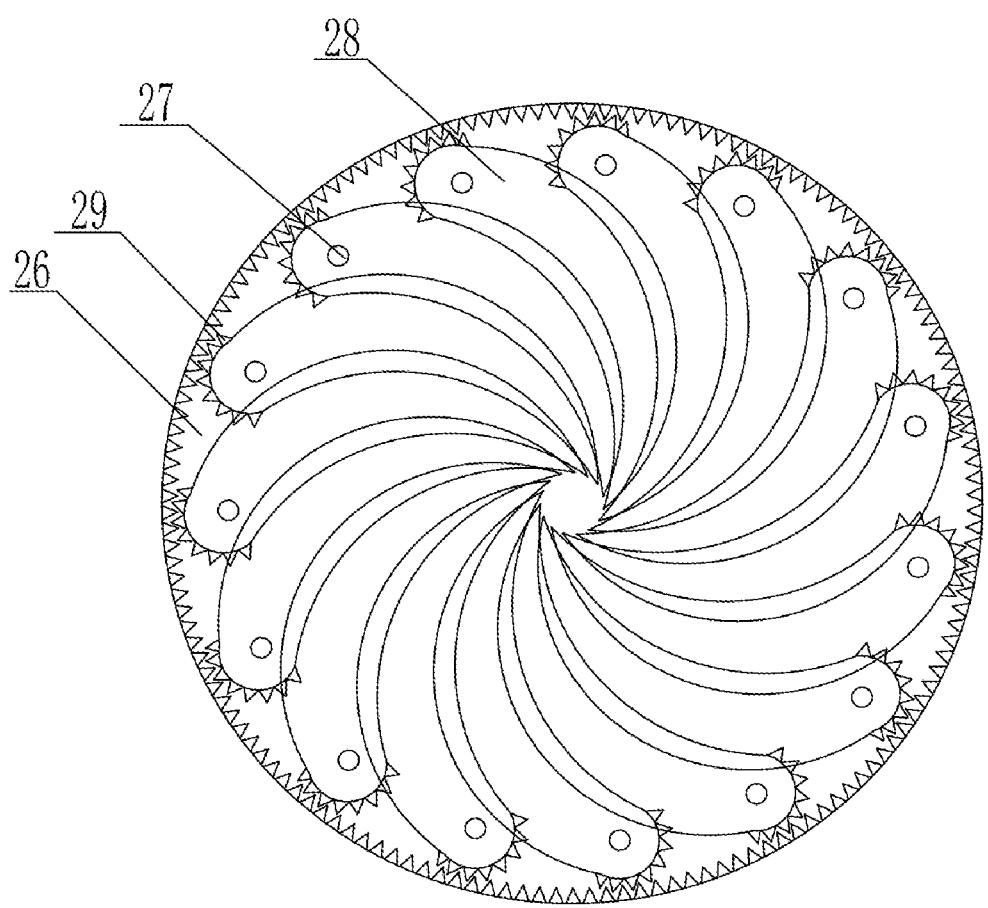
Figure 4:
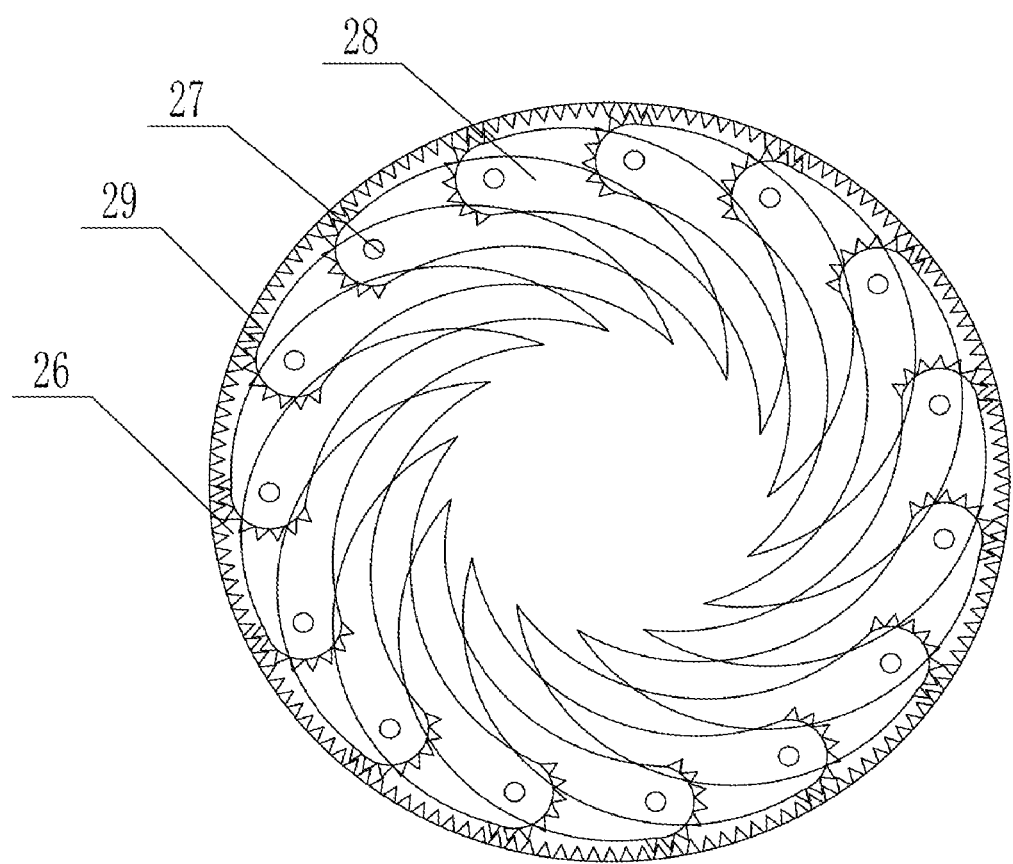
Figure 5:
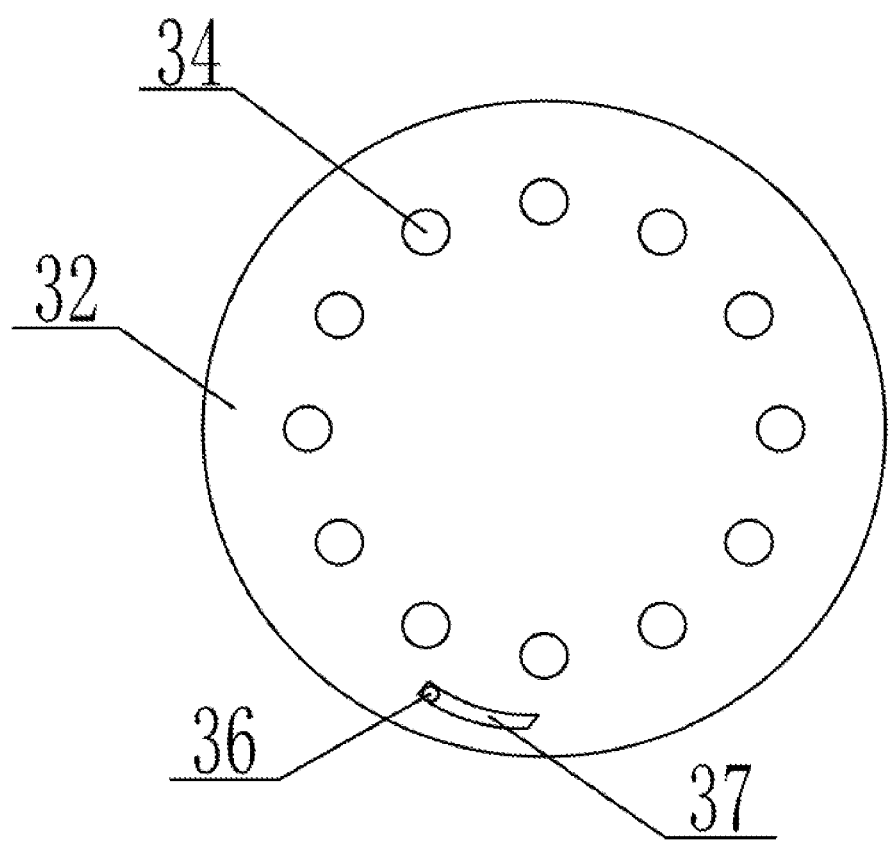
Figure 6:
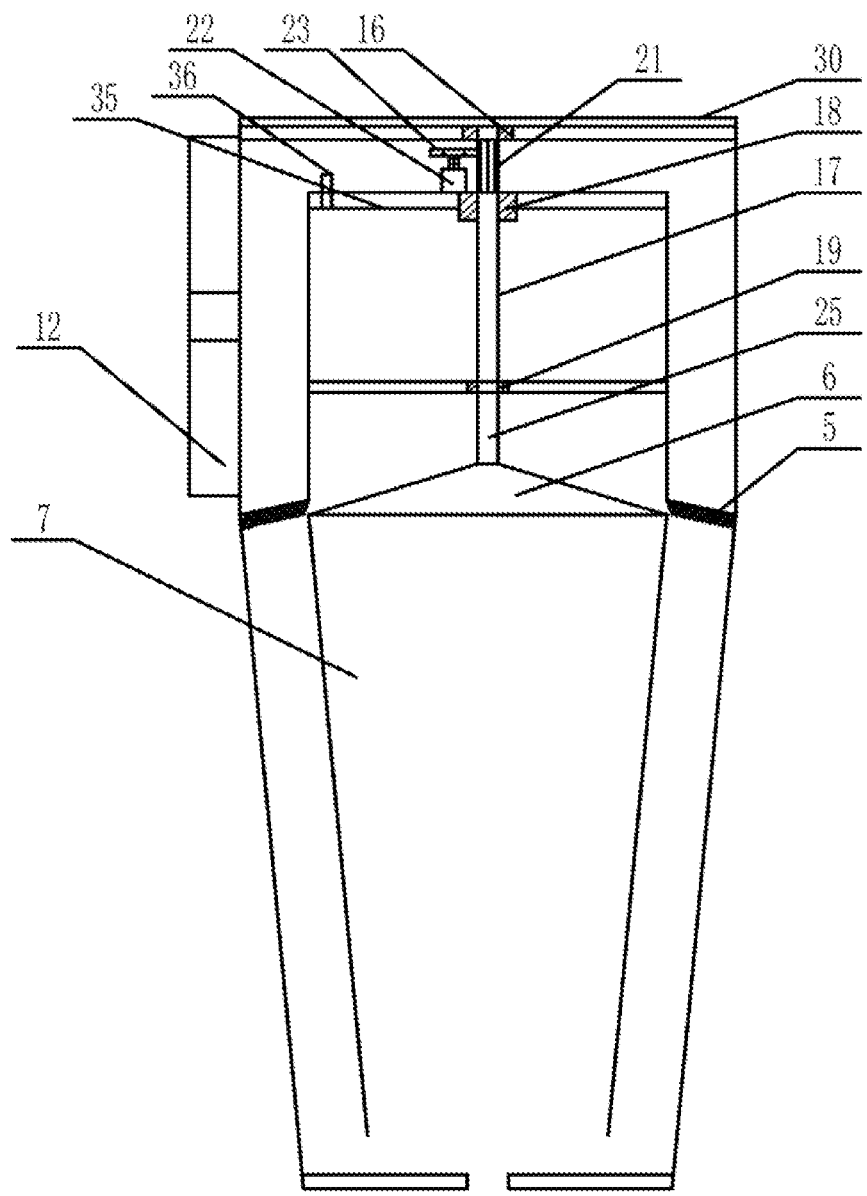
Figure 7:
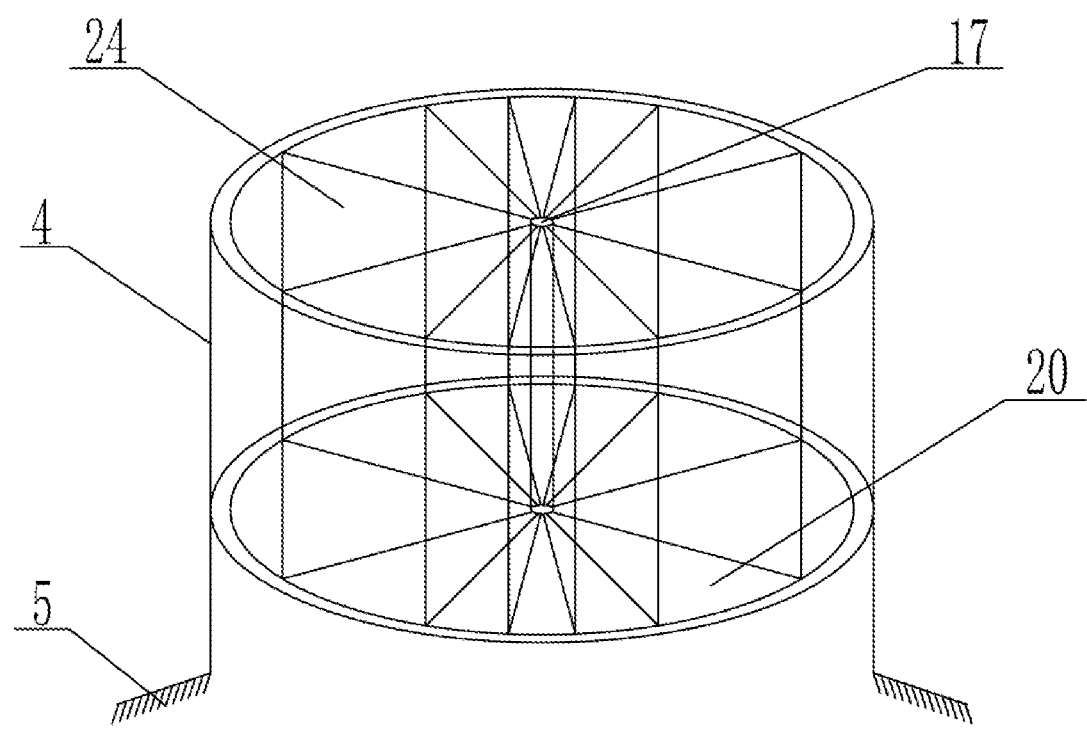
Figure 8:
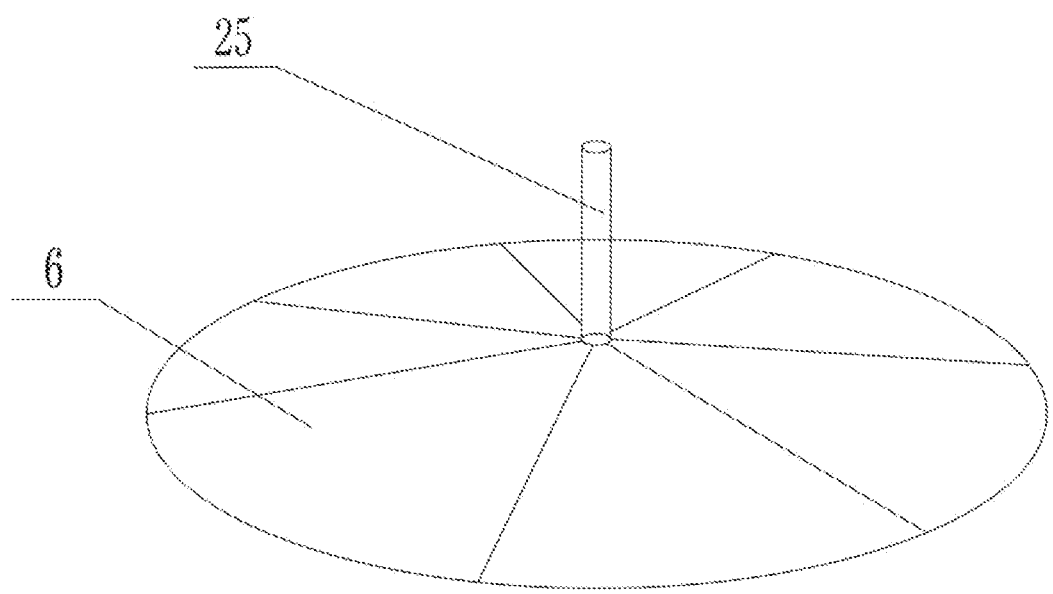
Figure 9:
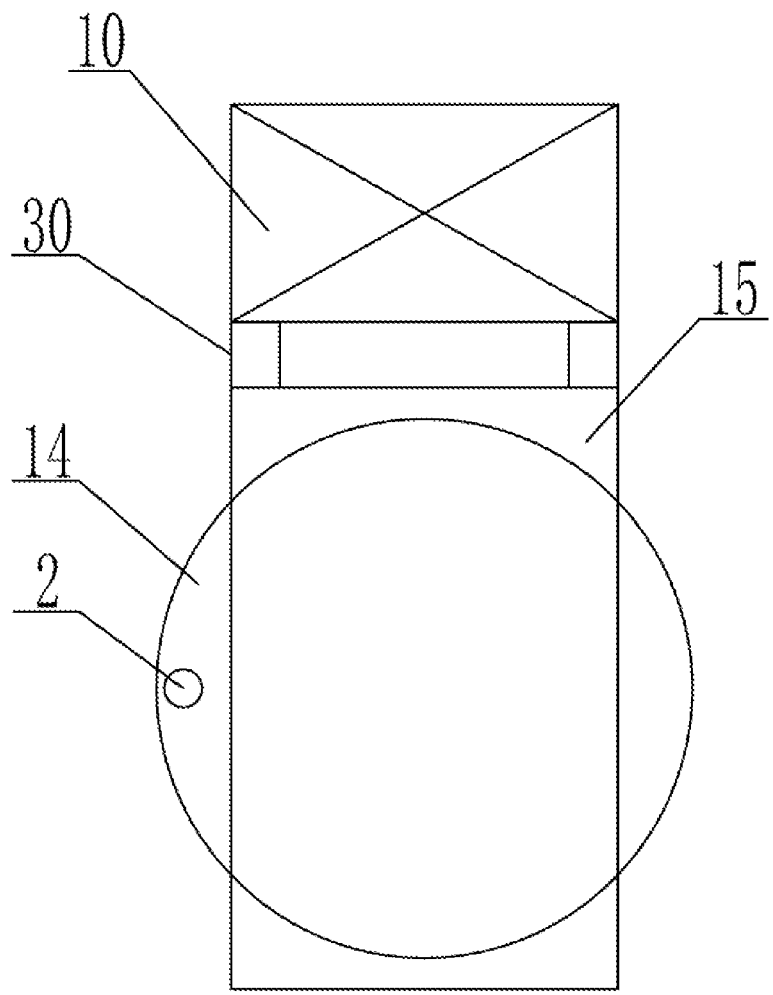

CN          113455377 A  * 10/2021
CN          113796308 A  * 12/2021

\* cited by examiner

POLLEN CONTROL DRY POLLINATION MACHINE FOR *ABIES ZIYUANENSIS*

CROSS-REFERENCE TO RELATED APPLICATIONS

This application claims priority to Chinese Patent Application No. 202210060272.5, filed on Jan. 19, 2022, the entire contents of which are incorporated herein by reference.

TECHNICAL FIELD

The present disclosure generally relates to plant pollination and breeding equipment, and in particular to a pollen control dry pollination machine for *Abies ziyuanensis*.

BACKGROUND

*Abies ziyuanensis* is a unisexual monoecious plant. Because most plants only develop ovulate strobiluses, namely female cones, only a few plants develop staminate strobiluses, namely male cones, and because individual distribution is scattered and distance between the plants is long, most ovulate strobiluses of the plants lack pollen sources and cannot be pollinated, resulting in serious seed abortion, further greatly limiting seedling regeneration and individual recruitment of wild populations, which is very unfavorable for this species to get out of endangered state. To alleviate this problem, it is necessary to artificially pollinate and breed the *Abies ziyuanensis* to obtain active seeds of this plant.

In a past, the *Abies ziyuanensis* was artificially pollinated mainly by brush dipping. The ovulate strobilus of the *Abies ziyuanensis*, inserted on a branch at a top of a crown, erect, cylindrical, sessile, with about 40 to 300 cone scales, a ventral base of each cone scale inserted with anatropous ovule. When pollinating, pollen is filled in a cone scale opening downwards, and the pollen tube contacts the anatropous ovule to complete pollination after germination. Owing to structure of the anatropous ovule, it is necessary to pollinate the ovulate strobilus repeatedly with a pollination pen, in order to make the pollen fully enter and adhere to the cone scale opening downwards, which is not only time-consuming, labor-intensive and inefficient, but also wastes pollen, thereby resulting in difficult pollination of *Abies ziyuanensis* on a large scale. Some existing spraying pollination devices for other plants are not developed for the ovulate strobilus with the anatropous ovule, so the pollen cannot enter the cone scale accurately, which not only leads to a low fertilization success rate, but also causes a large amount of pollen waste. Therefore, the existing spraying pollination devices are not suitable for large-scale pollination and breeding of *Abies ziyuanensis*. In order to improve the pollination success rate of *Abies ziyuanensis* and a utilization rate of the pollen, there is an urgent need for a pollen-controlled dry pollination machine which aims at the anatropous ovule of the *Abies ziyuanensis* and may save the pollen.

SUMMARY

An objective of the present application is to provide a pollen control dry pollination machine for *Abies ziyuanensis* to solve problems existing in prior art.

To achieve the above objective, the present application adopts the following technical schemes.

A pollen control dry pollination machine for *Abies ziyuanensis* includes a lever, a side of a top of the lever is fixedly connected with one end of a square tube, and another end of the square tube is rotatably connected with a pollination shell; a top of the square tube and a top of the pollination shell are slidably connected with a fan, and the fan is communicated with the pollination shell; the pollination shell is internally provided with a pollen box, a pollen outlet cover and a pollination chamber from a top to a bottom in sequence, and the pollen box is communicated with the pollen outlet cover; a bottom of the pollination chamber is provided with an opening, an *Abies ziyuanensis* ovulate strobilus to be pollinated is placed in the pollination chamber, and a bottom of the pollination shell is fixedly connected with a rotating opening; the lever is provided with a switch, and the switch is electrically connected with the fan.

Optionally, the pollen box is located at an inner top of the pollination shell, a bottom of a side wall of the pollen box is fixedly connected with a pollen blocking brush, an outer wall of the pollen blocking brush abuts against an inner wall of the pollination shell, a top of the pollen box is fixedly connected with a pollen cover, and a bottom of the pollen box is fixedly connected with the pollen outlet cover.

Optionally, the top of the pollination shell is embedded with a second bearing, and one end of a second connecting rod is fixedly connected in the second bearing; the pollen cover is communicated with the pollen box, a top surface of the pollen cover is embedded with a third bearing, and the second connecting rod passes through the third bearing and is located in the pollen box; the bottom of the pollen box is provided with a fourth bearing, the second connecting rod is embedded in the fourth bearing, and the bottom of the pollen box is provided with a pollen dropping port.

Optionally, teeth are arranged on the second connecting rod between the pollination shell and the pollen box, and a motor is fixedly connected to the top surface of the pollen cover, an output shaft of the motor is fixedly connected with a gear, the gear is meshed with the teeth, and the motor is electrically connected with the switch.

Optionally, a side wall of the second connecting rod located in the pollen box is fixedly connected with a number of baffles at equal intervals in a circumferential direction, and a cross-sectional area between two adjacent baffles is matched with an area of the pollen dropping port.

Optionally, the bottom of the pollen box is fixedly connected with one end of a third connecting rod, and another end of the third connecting rod is fixedly connected with a top surface of the pollen outlet cover; a gap exists between the pollen blocking brush and the pollen outlet cover, and a bottom surface of the pollen outlet cover is conical and fixedly connected with the pollination chamber.

Optionally, the rotating opening includes a first connecting plate fixedly connected to the bottom of the pollination shell, the first connecting plate is provided with a number of first through holes at equal intervals, the first through holes are penetrated with connecting columns, where each connecting column is movably connected with a rotating piece, an outer side of each rotating piece is sleeved with an internal gear disk, and the internal gear disks are matched with the rotating pieces.

Optionally, a first bearing is embedded in one end of the square tube close to the pollination shell, a bearing sleeve is fixedly connected to the top of the pollination shell, the bearing sleeve is located at one end of the pollination shell close to the square tube, and the bearing sleeve is embedded in the first bearing.

Optionally, a center of the bearing sleeve is provided with a connecting hole, one end of the first connecting rod is fixedly connected in the connecting hole, another end of the first connecting rod is fixedly connected with a rotating disk, two side walls of the square tube are provided with openings, the rotating disk is matched with the openings, outer edge of the rotating disk is located outsides the openings, and the rotating disk located outsides the openings is provides with a limiting protrusion.

Optionally, each top of the square tube and the pollination shell is fixedly connected with a slideway, a gap exists between the slideway on the top of the square tube and the slideway on the top of the pollination shell, and the slideways are slidably connected with the fan.

In this application, the lever is connected with the square tube, the switch is arranged on the lever, which is convenient for operators to use, and the pollination shell is rotatably connected with one end of the square tube far from the lever. When the *Abies ziyuanensis* tilts in a growth process, the pollination shell is rotated to adjust a pollination angle of the *Abies ziyuanensis*. The fan is slidably connected to the top of the square tube and the top of the pollination shell, so as to facilitate sliding of the fan, and thus facilitate adding the pollen into the pollen box. Wind in the fan enters the pollination shell through the top of the pollination shell, a gap exists between the pollination shell and the pollen box, a gap exists between the pollination shell and the pollination chamber, both gaps are pollen inlet channels, and the pollen blocking brush makes airflow in the pollen inlet channels stable, and prevents the pollen from blowing backwards. The pollen in the pollen box falls into the pollen inlet channel between the pollination chamber and the pollination shell through the pollen outlet cover communicated with the pollen box, is blown into the pollination chamber under an action of wind force, moves upward from a bottom of the pollination chamber by the airflow and easily enters a pistil under a cone scale of the *Abies ziyuanensis* ovulate strobilus, thus completing pollination. According to the present application, the rotating opening at the bottom of the pollination shell does not cause pollen waste, but also ensures pollination quality and improves pollination efficiency, so as to solve the problem of low efficiency of other pollination devices due to the structure of the ovulate strobilus of the *Abies ziyuanensis.*

BRIEF DESCRIPTION OF THE DRAWINGS

In order to more clearly explain the embodiments of the present application or the technical solutions in the prior art, the following will briefly introduce the drawings that need to be used in the embodiments. Obviously, the drawings in the following description are only some embodiments of the present application. For those of ordinary skill in the art, other drawings may be obtained according to these drawings without any creative effort.

FIG. 1 shows a schematic structural diagram of a pollen control dry pollination machine for *Abies ziyuanensis* in the present application.

FIG. 2 indicates a partial enlarged view of A in FIG. 1.

FIG. 3 shows a schematic structural diagram of a closed rotary switch.

FIG. 4 shows a schematic structural diagram of an opened rotary switch.

FIG. 5 shows a schematic structural diagram of a pollen cover.

FIG. 6 shows a schematic structural diagram of an inside of a pollen shell.

FIG. 7 shows a schematic structural diagram of an outside of a pollen shell.

FIG. 8 shows a schematic structural diagram of a pollen outlet cover.

FIG. 9 shows a schematic structural diagram of a rotating disk.

DETAILED DESCRIPTION OF THE EMBODIMENTS

The technical schemes of the present application will be clearly and completely described below with reference to the drawings, and it is clear that the described embodiments are a part of the embodiments of the present application, and not all of them. Based on the embodiments in the present application, all other embodiments obtained by a person of ordinary skill in the art without making creative labor fall within the scope of protection of the present application.

In order to make the above objective, features and advantages of the application obvious and understandable, the application is further explained in detail below with reference to the drawings and detailed description.

Referring to FIG. 1-FIG. 9, the present application adopts the following technical schemes.

A pollen control dry pollination machine for *Abies ziyuanensis* includes a lever 1, a side of a top of the lever 1 is fixedly connected with one end of a square tube 2, and another end of the square tube 2 is rotatably connected with a pollination shell 3; a top of the square tube 2 and a top of the pollination shell 3 are slidably connected with a fan 10, and the fan 10 is communicated with the pollination shell 3. The pollination shell 3 is internally provides with a pollen box 4, the pollen box 4 is located at an inner top of the pollination shell 3, a bottom of a side wall of the pollen box 4 is fixedly connected with a pollen blocking brush 5, and an outer wall of the pollen blocking brush 5 abuts against an inner wall of the pollination shell 3; a bottom of the pollen box 4 is fixedly connected with a pollen outlet cover 6, the pollen box 4 is communicated with the pollen outlet cover 6, and a bottom of the pollen outlet cover 6 is fixedly connected with a pollination chamber 7, where a diameter of the pollination chamber 7 is gradually reduced from a top to a bottom to adapt to a shape of *Abies ziyuanensis* ovulate strobilus. A bottom of the pollination chamber 7 is provided with an opening, the pollination chamber 7 is filled with the *Abies ziyuanensis* ovulate strobilus to be pollinated, a bottom of the pollination shell 3 is fixedly connected with a rotating opening 8, and carpopodium of the *Abies ziyuanensis* ovulate strobilus to be pollinated is located in the rotating opening 8. The lever 1 is provided with a switch 9, and the switch 9 is electrically connected with the fan 10.

The lever 1 is connected with the square tube 2, the switch 9 is arranged on the lever 1, which is convenient for operators to use, and the pollination shell 3 is rotatably connected with one end of the square tube 2 far from the lever 1. When the *Abies ziyuanensis* tilts in a growth process, the pollination shell 3 is rotated to adjust a pollination angle of the *Abies ziyuanensis*. The fan 10 is slidably connected to the top of the square tube 2 and the top of the pollination shell 3, so as to facilitate sliding of the fan 10, and thus facilitate adding the pollen into the pollen box 4. Wind in the fan 10 enters the pollination shell 3 through the top of the pollination shell 3, a gap exists between the pollination shell 3 and the pollen box 4, a gap exists between the pollination shell 3 and the pollination chamber 7, both gaps are pollen inlet channels, and the pollen blocking brush 5 makes airflow in the pollen inlet channels stable, and prevents the pollen from blowing backwards. The pollen in the pollen box 4 falls into the pollen inlet channel between the pollination chamber 7 and the pollination shell 3 through the pollen outlet cover 6 communicated with the pollen box 4, is blown into the pollination chamber 7 under an action of wind force, moves upward from a bottom of the pollination chamber 7 by the airflow and easily enters a pistil under a cone scale of the *Abies ziyuanensis* ovulate strobilus, thus completing pollination.

In an embodiment, the top of the pollination shell 3 is embedded with a second bearing 16, and one end of a second connecting rod 17 is fixedly connected in the second bearing 16; a pollen cover 32 is fixedly connected to an outside of the pollen box 4, the pollen cover 32 is communicated with the pollen box 4, a top surface of the pollen cover 32 is embedded with a third bearing 18, and the second connecting rod 17 passes through the third bearing 18 and is located in the pollen box 4; the bottom of the pollen box 4 is provided with a fourth bearing 19, the second connecting rod 17 is embedded in the fourth bearing 19, a top of the pollen box 4 is fixedly connected with the pollen cover 32, and the bottom of the pollen box 4 is provided with a pollen dropping port 20.

The second connecting rod 17 connects the pollen box 4 with the pollination shell 3, and enables the pollen box 4 to rotate.

In an embodiment, teeth 21 are arranged on the second connecting rod 17 between the pollination shell 3 and the pollen box 4, and a motor 22 is fixedly connected to the top surface of the pollen cover 32, an output shaft of the motor 22 is fixedly connected with a gear 23, the gear 23 is meshed with the teeth 21, and the motor 22 is electrically connected with the switch 9.

In an embodiment, a side wall of the second connecting rod 17 located in the pollen box 4 is fixedly connected with a number of baffles 24 at equal intervals in a circumferential direction, and a cross-sectional area between two adjacent baffles 24 is matched with an area of the pollen dropping port 20.

A pollen grid 33 is formed between the two adjacent baffles 24, and pollen inlets 34 are arranged on the pollen cover 32 at positions corresponding to each pollen grid 33. A bottom surface of the pollen cover 32 is rotatably connected with a wind shield 35, the wind shield 35 is provided with second through holes corresponding to the pollen inlets 34, the wind shield 35 is fixedly connected with a handle 36, the pollen cover 32 is provided with a chute 37, and the handle 36 is located in the chute 37 and extends out of the chute 37. When adding the pollen to the pollen grid 33, the fan 10 is slid to the top of the square tube 2, so that the handle 36 slides in the chute 37 and drives the wind shield 35 to rotate, the second through holes on the wind shield 35 correspond to the pollen inlets 34, and the pollen is added at this time. After adding, the handle 36 is reversely slid to block the pollen inlets 34, and the fan 10 is slid to the top of the pollination shell 3 and then started through the switch 9 to blow the pollen into the pollination chamber 7.

In an embodiment, the bottom of the pollen box 4 is fixedly connected with one end of a third connecting rod 25, and another end of the third connecting rod 25 is fixedly connected with a top surface of the pollen outlet cover 6; a gap exists between the pollen blocking brush 5 and the pollen outlet cover 6, a gap exists between the pollen outlet cover 6 and the pollination shell 3, the gap between the pollen outlet cover 6 and the pollination shell 3 is a pollen inlet channel, and a bottom surface of the pollen outlet cover 6 is conical, which is convenient for the pollen to fall into the pollen inlet channel.

In an embodiment, the rotating opening 8 includes a first connecting plate 26 fixedly connected to the bottom of the pollination shell 3, the first connecting plate 26 is provided with a number of first through holes at equal intervals, the first through holes are penetrated with connecting columns 27, each connecting column 27 is movably connected with a rotating piece 28, second teeth are arranged on an outer side of one end of each rotary piece 28 close to each connecting column 27, an outer side of each rotating piece 28 is sleeved with an internal gear disk 29, and the internal gear disks 29 are meshed with the second teeth.

When the *Abies ziyuanensis* ovulate strobilus is pollinated, the internal gear disks 29 are rotated by hand to drive the rotating pieces 28 meshed with the internal gear disks 29 to rotate, the rotating pieces 28 move to sides of the internal gear disks 29, so that the rotating opening 8 is gradually opened, the *Abies ziyuanensis* ovulate strobilus is placed in the pollination chamber 7, and the internal gear disks 29 are reversely rotated to gradually close the rotating opening 8 and just clamp the carpopodium without hurting the ovulate strobilus.

In an embodiment, a first bearing 11 is embedded in one end of the square tube 2 close to the pollination shell 3, a bearing sleeve 12 is fixedly connected to the top of the pollination shell 3, the bearing sleeve 12 is located at one end of the pollination shell 3 close to the square tube 2, and the bearing sleeve 12 is embedded in the first bearing 11.

In an embodiment, a center of the bearing sleeve 12 is provided with a connecting hole, one end of the first connecting rod 13 is fixedly connected in the connecting hole, another end of the first connecting rod 13 is fixedly connected with a rotating disk 14, two side walls of the square tube 2 are provided with openings, the rotating disk 14 is matched with the openings, the outer edge of the rotating disk 14 is located outsides of the openings, and the rotating disk 14 located the outsides of the openings is provided with a limiting protrusion 15.

When an angle of the pollination shell 3 is adjusted, the rotating disk 14 is turned by hand to drive the first connecting rod 13 to rotate, and the first connecting rod 13 drives the bearing sleeve 12 fixedly connected with the first connecting rod 13 to rotate, and further drives the pollination shell 3 to rotate. In addition, the limiting protrusion 15 limits the rotating disk 14, so as to prevent an excessive rotation angle of the rotating disk from causing negative effects on the pollination.

In an embodiment, each top of the square tube 2 and the pollination shell 3 is fixedly connected with a slideway 30, a gap exists between the slideway 30 on the top of the square tube 2 and the slideway 30 on top of the pollination shell 3, and the slideways 30 are slidably connected with the fan 10, which is convenient for the pollination shell 3 to rotate.

In an embodiment, a bottom of the lever 1 is provided with a storage battery 31, the storage battery 31 is electrically connected with the switch 9 and the motor 22 respectively.

Working principle of the present application is as follows.

The internal gear disks 29 are rotated by hand to drive the rotating pieces 28 meshed with the internal gear disks 29 to rotate, the rotating pieces 28 move to the sides of the internal gear disks 29, so that the rotating opening 8 is gradually opened, the *Abies ziyuanensis* ovulate strobilus is placed in the pollination chamber 7, and the internal gear disks 29 are reversely rotated to gradually close the rotating opening 8 and just clamp the carpopodium without hurting the ovulate strobilus. The fan 10 is slid to the top of the square tube 2, so that the handle 36 slides in the chute 37 and drives the wind shield 35 to rotate, the second through holes on the wind shield 35 correspond to the pollen inlets 34, and the pollen is added at this time. After adding, the handle 36 is reversely slid to block the pollen inlets 34, the fan 10 is slid to the top of the pollination shell 3, and the motor 22 is started by the switch 9. The motor 22 drives the gear 23 to rotate, the gear 23 drives the second connecting rod 17 meshed with the gear 23 to rotate, and the second connecting rod 17 drives the baffles 24 to rotate, so that the baffles 24 correspond to the pollen dropping port 20, and thereby the pollen falls into a top surface of the pollen outlet cover 6 along the pollen dropping port 20 and falls into the pollen inlet channel along the pollen outlet cover 6. The fan 10 is started by the switch 9 and blows the pollen into the pollination chamber 7, and the pollen moves upward from the bottom of the pollination chamber 7 by the airflow and easily enters the pistil under the cone scale. After the pollination, the internal gear disks 29 are rotated to drive the rotating pieces 28 meshed with the internal gear disks 29 to rotate to the sides of the internal gear disks 29, so that the rotating opening 8 is gradually opened, and the pollinated *Abies ziyuanensis* ovulate strobilus is taken out to complete the pollination.

In the description of the present application, it should be understood that the orientation or positional relationship indicated by terms "longitudinal", "transverse", "upper", "lower", "front", "rear", "left", "right", "vertical", "horizontal", "top", "bottom", "inner", "outer", etc. is based on the orientation or positional relationship shown in the drawings, and is only for the convenience of describing the present application, rather than indicating or implying that the device or element referred to must have a particular orientation, be constructed and operate in a particular orientation, and therefore should not be understood as limiting the application.

It should be understood that the technical schemes of the present application are not limited to the limits of the above specific embodiments, and any technical variations made according to the technical solutions of the present application, without departing from the scope protected by the objective and claims of the present application, fall within the scope of protection of the present application.

The invention claimed is:

1. A pollen control dry pollination machine for *Abies ziyuanensis*, comprising a lever, wherein a side of a top of the lever is fixedly connected with one end of a square tube, and another end of the square tube is rotatably connected with a pollination shell; a top of the square tube and a top of the pollination shell are slidably connected with a fan, and the fan is communicated with the pollination shell; the pollination shell is internally provided with a pollen box, a pollen outlet cover and a pollination chamber from a top to a bottom in sequence, wherein the pollen box is communicated with the pollen outlet cover; a bottom of the pollination chamber is provided with an opening, an *Abies ziyuanensis* ovulate strobilus to be pollinated is placed in the pollination chamber, and a bottom of the pollination shell is fixedly connected with a rotating opening; the lever is provided with a switch, and the switch is electrically connected with the fan;

the pollen box is located at an inner top of the pollination shell, a bottom of a side wall of the pollen box is fixedly connected with a pollen blocking brush, an outer wall of the pollen blocking brush abuts against an inner wall of the pollination shell, a top of the pollen box is fixedly connected with a pollen cover, and a bottom of the pollen box is fixedly connected with the pollen outlet cover;

the top of the pollination shell is embedded with a second bearing, and one end of a second connecting rod is fixedly connected in the second bearing; the pollen cover is communicated with the pollen box, a top surface of the pollen cover is embedded with a third bearing, and the second connecting rod passes through the third bearing and is located in the pollen box; the bottom of the pollen box is provided with a fourth bearing, the second connecting rod is embedded in the fourth bearing, and the bottom of the pollen box is provided with a pollen dropping port;

teeth are arranged on the second connecting rod between the pollination shell and the pollen box, and a motor is fixedly connected to the top surface of the pollen cover, an output shaft of the motor is fixedly connected with a gear, the gear is meshed with the teeth, and the motor is electrically connected with the switch;

a side wall of the second connecting rod located in the pollen box is fixedly connected with a number of baffles at equal intervals in a circumferential direction, and a cross-sectional area between two adjacent baffles is matched with an area of the pollen dropping port;

the bottom of the pollen box is fixedly connected with one end of a third connecting rod, and another end of the third connecting rod is fixedly connected with a top surface of the pollen outlet cover; a gap exists between the pollen blocking brush and the pollen outlet cover, and a bottom surface of the pollen outlet cover is conical and fixedly connected with the pollination chamber;

the rotating opening comprises a first connecting plate fixedly connected to the bottom of the pollination shell, the first connecting plate is provided with a number of first through holes at equal intervals, the first through holes are penetrated with connecting columns, wherein each connecting column is movably connected with a rotating piece, an outer side of each rotating piece is sleeved with an internal gear disk, and the internal gear disks are matched with the rotating pieces;

a first bearing is embedded in one end of the square tube close to the pollination shell, a bearing sleeve is fixedly connected to the top of the pollination shell, the bearing sleeve is located at one end of the pollination shell close to the square tube, and the bearing sleeve is embedded in the first bearing;

a center of the bearing sleeve is provided with a connecting hole, one end of the first connecting rod is fixedly connected in the connecting hole, another end of the first connecting rod is fixedly connected with a rotating disk, two side walls of the square tube are provided with openings, wherein the rotating disk is matched with the openings, outer edge of the rotating disk is located outsides the openings, and the rotating disk located outsides the openings is provides with a limiting protrusion; and each top of the square tube and the pollination shell is fixedly connected with a slideway, wherein a gap exists between the slideway on the top of the square tube and the slideway on the top of the pollination shell, and the slideways are slidably connected with the fan.

* * * * *